United States Patent
Gilbert

(10) Patent No.: US 6,508,391 B2
(45) Date of Patent: Jan. 21, 2003

(54) MEDICAL STORAGE POUCH

(76) Inventor: Patricia A. Gilbert, 3715 Clarks Point Rd., Middle River, MD (US) 21220

( * ) Notice: Subject to any disclaimer, the term of this patent is extended or adjusted under 35 U.S.C. 154(b) by 1 day.

(21) Appl. No.: 09/846,210

(22) Filed: May 2, 2001

(65) Prior Publication Data
US 2002/0162873 A1 Nov. 7, 2002

(51) Int. Cl.⁷ .................................................. A45C 1/04
(52) U.S. Cl. ....................... 224/664; 224/677; 224/245; 224/251; 224/901.6
(58) Field of Search .................................... 224/660, 664, 224/677, 235, 245, 250, 251, 901.6

(56) References Cited

U.S. PATENT DOCUMENTS

| | | | | |
|---|---|---|---|---|
| 2,399,040 A | * | 4/1946 | Karle ........................ 206/227 |
| 4,079,767 A | * | 3/1978 | Howard ....................... 224/235 |
| 4,343,158 A | | 8/1982 | Campbell |
| 4,368,642 A | | 1/1983 | Carodiskey |
| 4,738,364 A | | 4/1988 | Yeager |
| 4,796,790 A | | 1/1989 | Hamilton |
| 5,024,361 A | * | 6/1991 | Flowers ...................... 224/223 |
| 5,135,144 A | | 8/1992 | Blakely et al. |
| 5,154,324 A | | 10/1992 | Stratford |
| 5,169,043 A | * | 12/1992 | Catania ...................... 224/660 |
| 5,411,193 A | | 5/1995 | Culp |
| 5,540,366 A | * | 7/1996 | Coomber ..................... 224/587 |
| 5,577,653 A | * | 11/1996 | Bieker ...................... 224/148.1 |
| 5,584,386 A | | 12/1996 | Ahonen |
| 5,708,978 A | | 1/1998 | Johnsrud |
| 5,816,459 A | | 10/1998 | Armistead |
| 5,865,314 A | | 2/1999 | Jacober |
| 5,873,504 A | | 2/1999 | Farmer |
| 5,893,370 A | | 4/1999 | Perez et al. |
| 5,911,709 A | | 6/1999 | Hogan |
| 5,940,883 A | | 8/1999 | Daoust |
| 6,109,496 A | | 8/2000 | Andrew et al. |
| 6,296,164 B1 | * | 10/2001 | Russo ........................ 224/581 |
| 6,405,912 B2 | * | 6/2002 | Giannou ..................... 224/233 |

* cited by examiner

Primary Examiner—Stephen K. Cronin
(74) Attorney, Agent, or Firm—Rosenberg, Klein & Lee

(57) ABSTRACT

A medical storage pouch (10) is provided. The medical storage pouch (10) includes a bag member (14) having a belt member (16) permanently affixed thereto, allowing the bag member (14) to be worn around the waist of a user (12). Bag member (14) includes a releasable closure means (26). Fixed to an inner wall of inner compartment (24) within bag member (14) is a retaining strap (36). Retaining strap (36) removably receives an elongated container (28). Elongated container (28) includes a cap member (34) and has a recess (30) formed therein for receiving a syringe or other container (32). Bag member (14) and elongated container (28) provide protection and insulation for syringe or container (32).

19 Claims, 3 Drawing Sheets

MEDICAL STORAGE POUCH

BACKGROUND OF THE INVENTION

1. Field of the Invention

The subject invention relates to a medical storage pouch providing transportation and protection of medical supplies. In particular, the present invention directs itself to a storage pouch having an adjustable belt fixed thereto for securement around the waist of a user. More particularly, this invention directs itself to a medical storage pouch having an interior compartment designed to removably receive an elongated container.

The subject invention is further directed to a medical storage pouch having an elongated container with an inner chamber formed therein for receiving a syringe or other medical container.

Further, the subject invention relates to a medical storage pouch having an opening sealed by a closure. On either side of the opening are fabric loops allowing for the easy opening of the medical storage pouch.

2. Prior Art

Medical storage pouches are known in the art. In general, such prior art pouches include some type of flexible bag member having a belt or attached clip. In many instances, the problems of such prior art pouches are that the pouches are designed primarily for the transportation of medical supplies and not for the protection of the medical supplies. Syringes and containers for medicine must be protected from physical shock, excessive temperature, water, and other environmental hazards. It is a purpose of the subject invention to provide a combination of elements making up a medical storage pouch which provides for both ease of transportation of medical supplies and the protection of the medical supplies.

One such prior art pouch is shown in U.S. Pat. No. 4,343,158. This reference is directed to a portable pouch for insulin. The pouch includes a flexible bag member having an opening and an attached closure means. Although the bag member provides minimal padding for syringes and included insulin vials, the syringes and vials are not provided the necessary protection from physical shock that such fragile containers require. Additionally this prior art pouch does not include an additional container for the syringes or vials.

Another such prior art pouch is shown in U.S. Pat. No. 4,796,790. This reference is directed to a medical supply case. The case includes a pouch having multiple pockets and a means for hanging from a user's belt. Medical supplies including syringes, are stored in the pockets. However, no additional container for the syringes or other vials of medicine is provided.

U.S. Pat. No. 6,109,496 is directed to a hip-carried bag for electrical equipment including radio transceivers. This reference includes a bag having an adjustable belt affixed thereto and to be worn about the waist region of a user, although the bag does not include an additional container for medical supplies or the like.

U.S. Pat. No. 5,411,193 is directed to a portable containment device for contaminated medical objects. This reference includes a bag member worn on the belt of a user. Although the bag member itself provides protection to the environment from the enclosed syringes, it does not provide an additional container, held within the bag member, for holding the syringes.

Another prior art medical supply transportation system is shown in U.S. Pat. No. 5,940,883. This reference is directed to a veterinarian vest/belt assembly. A belt assembly is provided for the storage of various medical storage pouch supplies and tools. The belt includes pockets and attachments, however, does not include additional containers for the protection of medical supplies.

None of the prior art provides for a combination of elements forming a medical supply pouch having an additional elongated container for the storage and protection of medical supplies. Due to the fragile nature of syringes, vials of medicine, and the like, an additional container is necessary for providing protection from physical shock, temperature, water, and other environmental dangers.

SUMMARY OF THE INVENTION

The present invention provides for a medical storage pouch adapted to be worn around the waist of a user. The medical storage pouch includes an adjustable belt member having a clasp for removable wear around the waist of a user. Further, the medical storage pouch includes a main bag member formed with an opening, the opening being sealed by a closure. A pair of loop members are provided adjacent the opening of the bag member for ease in opening of the bag.

Further, the interior of the bag member has at least one loop fixed therein for removably receiving an elongated container. The elongated container is formed of a resilient material and has a recess or inner chamber formed therein for the reception of a syringe or other medical storage container.

It is a principal objective of the medical storage pouch to provide a storage bag member having an affixed adjustable belt which may be worn about the waist of a user. It is a further objective of the subject medical storage pouch to provide a bag member having an opening, the opening being sealed by a closure. It is a further objective of the medical storage pouch to provide a pair of loops adjacent the opening of the bag member for effectuating the opening of the storage pouch. It is a further objective of the subject medical storage pouch to provide at least one retaining strap within the interior of the bag member for removably receiving an elongated container.

It is an important objective of the present invention to provide an elongated container having a recess formed therein for receiving a syringe or other medical container in order to protect the syringe or container from physical shock, temperature, water, or other environmental hazards.

DESCRIPTION OF THE PREFERRED EMBODIMENTS

Figure 1:
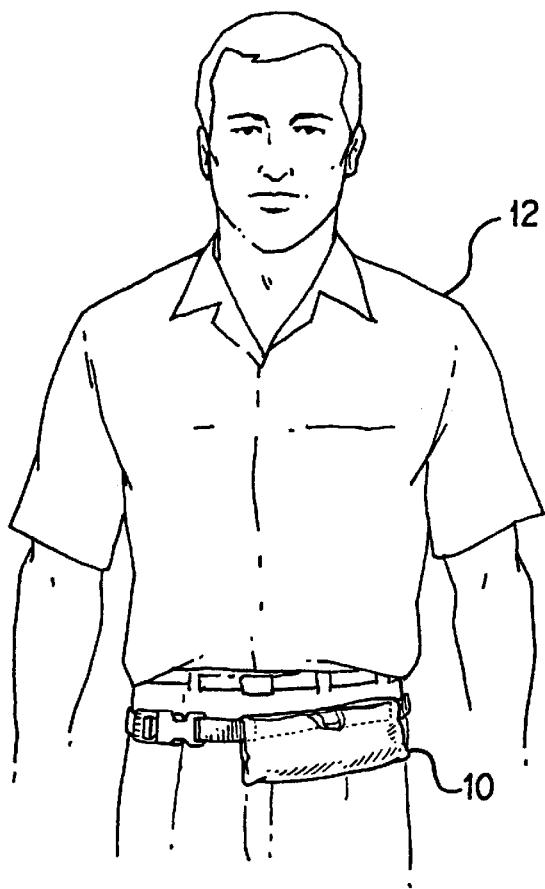
FIG. 1 is a perspective view of the subject medical storage pouch worn around the waist of a user.
Figure 2:
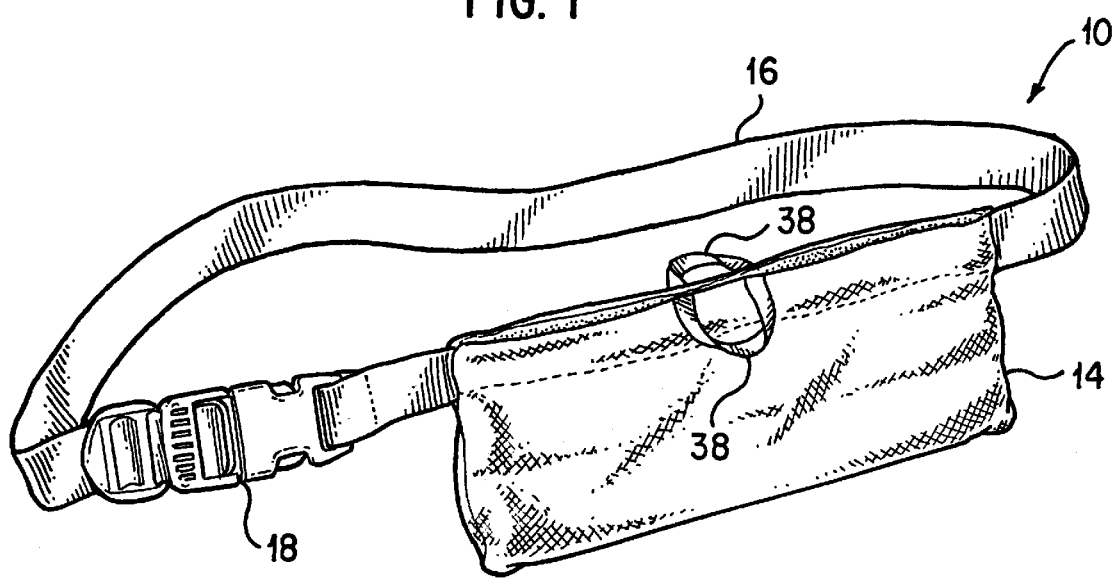
FIG. 2 is a perspective view of the medical storage pouch in its closed state.

Referring to FIGS. 1–6, there is shown a medical storage pouch 10 which is worn by a user 12 to transport, contain and protect medical supplies. As shown in FIG. 2 of the Drawings, the medical storage pouch 10 includes a bag member 14 having a belt member 16 affixed thereto.

The belt member 16, as shown in FIG. 2, is adjustable in length and includes a clasp member 18 for ease of removal. Belt 16 may be made of any suitable material, including fabric, plastic, leather, or the like.

Figure 3:
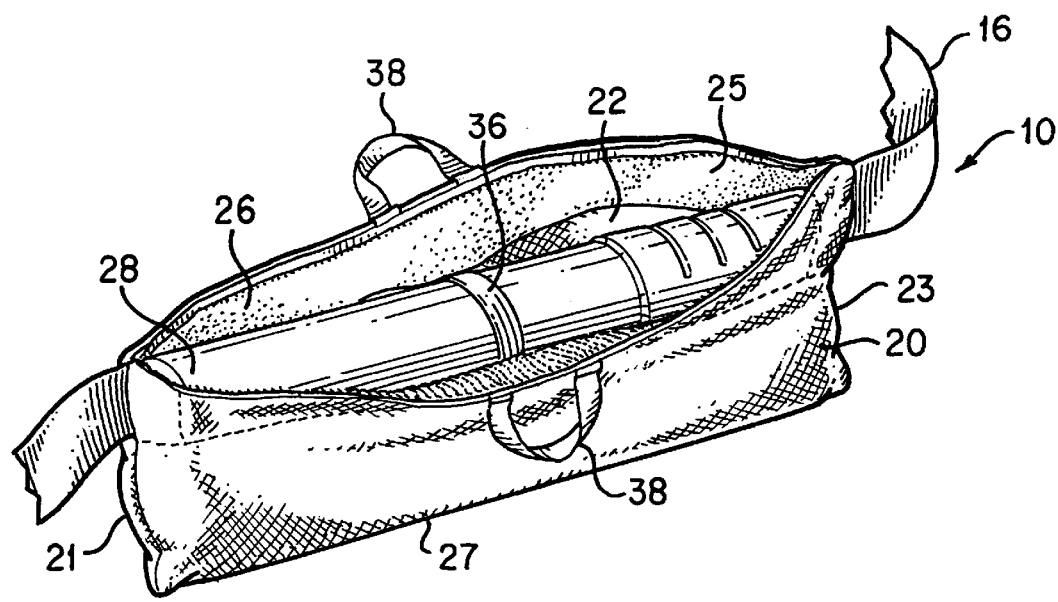
FIG. 3 is a perspective view of the medical storage pouch in its opened state.
Figure 4:
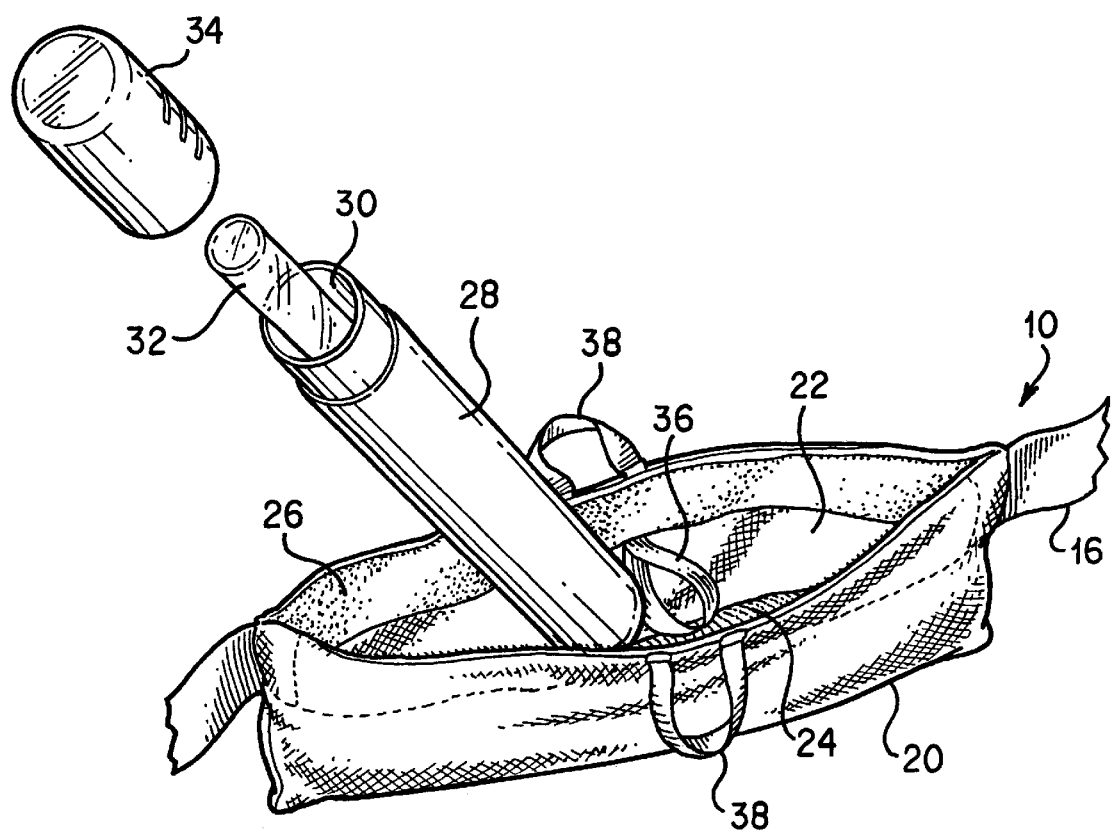
FIG. 4 is an exploded view of the medical storage pouch in an open state prior to insertion of an elongated container.

As shown in FIGS. 3 and 4, the bag member 14 of the medical storage pouch 10 is formed from first wall 20 and second wall 22. First and second walls 20 and 22 may be formed from fabric, plastic, or any other resilient, thermally insulating, waterproof material. Preferably, walls 20 and 22 are formed of a material having a relatively low thermal conductivity to impede heat transport.

As best shown in FIG. 3, each of the first and second walls 20 and 22 includes a pair of laterally opposed side edges 21, 23 and a bottom edge 27. The side edges 21, 23 and the bottom edges 27 of the first and second walls 20, 22 are permanently joined to one another by stitching, heat sealing, or any other suitable means for permanently joining the two walls to one another.

As shown in FIGS. 3 and 4, the first and second walls 20, 22 form an inner compartment 24 having an opening 25. Opening 25 is releasably sealed by closure 26. Closure 26 may be a hook-and-loop type fastener, a zipper, snaps, buttons, or any other suitable releasable closure mechanism.

External loops 38 are provided on each of the first and second walls 20, 22 near opening 25. External loops 38 are permanently fixed to first and second walls 20, 22 by stitching, heat sealing, or any other suitable means. External loops 38 allow a user 12 to easily open the medical storage pouch 10 when closure means 26 is used to seal the inner compartment 24. External loops 38 are sized to receive the fingers of the user 12.

As best shown in FIG. 4, an elongated container 28 is removably received within inner compartment 24 of the bag member 14. The elongated container 28 has a recess 30 or inner chamber formed therein for receiving a syringe or container 32. A cap member 34 is provided for releasable sealing of the inner chamber 30 in elongated container 28.

The elongated container 28 is formed from an insulating, resilient and waterproof material, such as plastic, rubber, or some like composition. Container 30 receives syringe or container 32. The syringe or container 32 is generally formed from a fragile material, such as glass, and contains therein medical supplies however in some instances container 32 may be formed of a rigid composition such as plastic or metal. Elongated container 28 provides protection for a fragile syringe or container 32 from physical shock, temperature, water, and other environmental hazards.

As shown in FIG. 4, a retaining strap 36 is fixed to one of the walls 20, 22 within inner compartment 24. As shown in FIG. 3, the retaining strap 36 receives the elongated container 28, holding it in place within the inner compartment 24 of the medical storage pouch 10.

Figure 5:
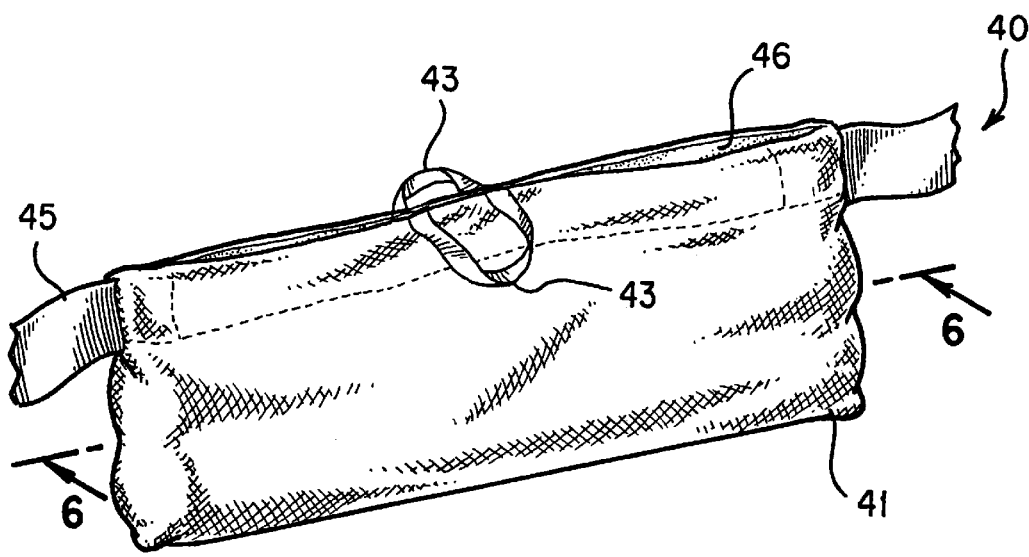
FIG. 5 is a perspective view of an alternative embodiment of the medical storage pouch; and, FIG. 6 is a cross-sectional view of an alternative embodiment of the medical storage pouch taken along the section line 6—6 of FIG. 5.
Figure 6:
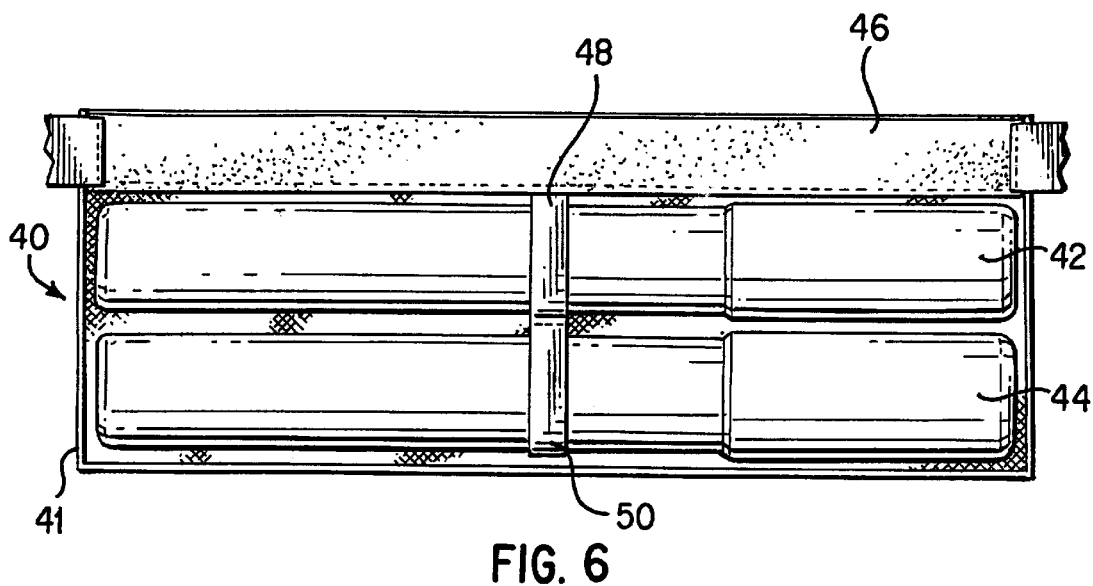

FIGS. 5 and 6 illustrate an alternative embodiment wherein medical storage pouch 40 receives both a first container 42 and a second container 44. As shown in FIG. 5, the medical storage pouch 40 includes a bag member 41 which is releasably sealed by closure means 46. A belt member 45 is permanently joined to bag member 41. Additionally, external loops 43 are permanently affixed to the bag member 41 near the opening for effectuating opening of the medical storage pouch 40. As shown in FIG. 6, medical storage pouch 40 includes first and second containers 42, 44 releasably held within the interior of the bag member 41 by first and second retaining straps 48, 50. The medical storage pouch 40 further includes a closure means 46.

Although FIG. 6 illustrates an embodiment of the medical storage pouch wherein two containers 42, 44 are held within the interior of the bag member 41, medical storage pouches 40 may be adapted to receive any number of elongated containers.

The medical storage pouches 10, 40 include elongated containers 28, 42, and 44, respectively. These containers are composed of resilient, insulating and waterproof materials and are designed to receive syringes or other medical containers therein. Syringes and medical vials are often made of glass and other fragile materials and contain medicines which are susceptible to heat and moisture. The containers 28, 42, and 44, respectively, provide for additional protection of the fragile syringes or vials 32.

Although this invention has been described in connection with specific forms and embodiments thereof, it will be appreciated that various modifications other than those discussed above may be resorted to without departing from the spirit or scope of the invention. For example, functionally equivalent elements may be substituted for those specifically shown and described without departing from the spirit or scope of the invention as defined in the appended claims.

What is claimed is:

1. A medical storage pouch comprising:
a flaccid, elongated bag member having an opening and a pair of walls defining an inner compartment;
a closure for releasably sealing said walls of said inner compartment, said opening having a pair of loops affixed thereto, said loops effectuating the unsealing of said walls defining said inner compartment;
a belt member affixed to said bag, said belt member adapted to be worn around the waist of a user; and,
at least one elongated container for storing medicine, said container being removably coupled to one of said pair of walls within said inner compartment.

2. The medical storage pouch as recited in claim 1 wherein said closure is a hook-and-loop fastener.

3. The medical storage pouch as recited in claim 1 wherein said belt has an adjustable length.

4. The medical storage pouch as recited in claim 1 wherein said belt has a clasp.

5. The medical storage pouch as recited in claim 1 wherein said elongated container is a cylindrical tube, said cylindrical tube defining an inner chamber adapted for storing medicine.

6. The medical storage pouch as recited in claim 5 wherein said elongated container includes a cap member for releasably covering and sealing said inner chamber.

7. The medical storage pouch as recited in claim 1 wherein said elongated container is formed of a resilient material.

8. The medical storage pouch as recited in claim 1 wherein at least one of said pair of walls has at least one retaining strap affixed thereto, said retaining strap adapted to receive said elongated container.

9. The medical storage pouch as recited in claim 1 wherein said flaccid, elongated bag is formed of a thermally insulating material.

10. A medical storage pouch comprising:
a flaccid, elongated bag member having an opening and a pair of walls defining an inner compartment;
a closure for releasably sealing said walls of said inner compartment;

a pair of loops fixed to said flaccid, elongated bag member adjacent said opening for effectuating the unsealing of said opening;

a belt member affixed to said bag, said belt member adapted to be worn around the waist of a user; and, at least one elongated container for storing medicine, said container being removably held to one of said pair of walls within said inner compartment.

11. The medical storage pouch as recited in claim 10 wherein said closure is a hook-and-loop fastener.

12. The medical storage pouch as recited in claim 10 wherein said belt has an adjustable length.

13. The medical storage pouch as recited in claim 10 wherein said belt has a clasp.

14. The medical storage pouch as recited in claim 10 wherein said elongated container is a cylindrical tube, said cylindrical tube defining a recess adapted for storing medicine.

15. The medical storage pouch as recited in claim 14 wherein said elongated container includes a cap member for releasably covering and sealing said recess.

16. The medical storage pouch as recited in claim 10 wherein said elongated container is formed of a resilient material.

17. The medical storage pouch as recited in claim 10 wherein at least one of said pair of walls has at least one retaining strap affixed thereto, said retaining strap adapted to receive said elongated container.

18. The medical storage pouch as recited in claim 10 wherein said flaccid, elongated bag is formed of a thermally insulating material.

19. The medical storage pouch as recited in claim 10 wherein said pair of loops are formed of a resilient material.

* * * * *